United States Patent
Song et al.

(10) Patent No.: US 10,023,915 B2
(45) Date of Patent: Jul. 17, 2018

(54) METHOD FOR SCREENING FOR A CANCER TREATMENT AGENT USING THE INTERACTION BETWEEN PAUF AND A BINDING PARTNER THEREOF

(75) Inventors: Si Young Song, Seoul (KR); Sun A Kim, Seoul (KR); Soo Bin Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 124 days.

(21) Appl. No.: 14/008,537

(22) PCT Filed: Aug. 2, 2011

(86) PCT No.: PCT/KR2011/005684
§ 371 (c)(1),
(2), (4) Date: Sep. 27, 2013

(87) PCT Pub. No.: WO2012/133994
PCT Pub. Date: Oct. 4, 2012

(65) Prior Publication Data
US 2014/0018304 A1    Jan. 16, 2014

(30) Foreign Application Priority Data
Mar. 28, 2011 (KR) .......... 10-2011-0027472

(51) Int. Cl.
| | | |
|---|---|---|
| C12Q 1/68 | (2018.01) | |
| G01N 33/15 | (2006.01) | |
| C12Q 1/6886 | (2018.01) | |
| G01N 33/574 | (2006.01) | |
| G01N 33/68 | (2006.01) | |

(52) U.S. Cl.
CPC ..... *C12Q 1/6886* (2013.01); *G01N 33/57438* (2013.01); *G01N 33/6893* (2013.01); *G01N 2333/4706* (2013.01)

(58) Field of Classification Search
None
See application file for complete search history.

(56) References Cited

U.S. PATENT DOCUMENTS

| | | |
|---|---|---|
| 5,840,870 A | 11/1998 | Goold et al. |
| 5,998,165 A | 12/1999 | Goold et al. |
| 2009/0188000 A1 | 7/2009 | Koh et al. |
| 2009/0291441 A1* | 11/2009 | Zheng .............. 435/6 |
| 2011/0104658 A1* | 5/2011 | Prabhakarpandian ............ G01N 33/5029 435/5 |
| 2012/0015847 A1 | 1/2012 | Kim |
| 2014/0239169 A1* | 8/2014 | Robinson ......... G01N 33/6848 250/282 |
| 2015/0101070 A1* | 4/2015 | Nam ............... G01N 33/5011 800/3 |

FOREIGN PATENT DOCUMENTS

WO    WO2010/036031    *   4/2010

OTHER PUBLICATIONS

Baxevanis (Expert Opinion: Drug Discovery, vol. 3, No. 4, p. 441-452, 2008).*
Montrose-Rafizadeh (The Journal of Biological Chemistry, vol. 272, p. 21201-21206, 1997).*
Rodems (Assay and Drug Development Technologies, vol. 1, No. 1-1, p. 9-19, 2002).*
Wall et Al., Theriogenology, vol. 45, p. 57-68, 1996.*
Houdebine et Al., Journal of Biotechnology, vol. 34, p. 269-287, 1994.*
Kappell et Al., Current Opinions in Biotechnology, vol. 3, p. 548-553, 1992.*
International Search Report for PCT/KR2011/005684.
Lee Y. et al. PAUF functions in the metastasis of human pancreatic cancer cells and upregulates CXCR4 expression. Oncogene. 2010, vol. 29, No. 1, figures 56-67.
Fujioka S. et al. Function of nuclear factor kB in pancreatic cancer metastasis. Clinical Cancer Research. 2003, vol. 9, figures 346-54.

* cited by examiner

*Primary Examiner* — Michael Allen
(74) *Attorney, Agent, or Firm* — Harness, Dickey & Pierce, P.L.C.

(57) ABSTRACT

The present invention relates to a method for screening for a cancer treatment agent by contacting a test material with pancreatic adenocarcinoma upregulated factor (PAUF) and GLRX3, SNAPIN, or UBL4A, as a binding partner for PAUF, and then analyzing whether or not the test material inhibits the binding of the PAUF and GLRX3, SNAPIN, or UBL4A serving as a binding partner therefor, thereby determining that the test material is a cancer treatment agent if the binding is inhibited. The invention also relates to a pharmaceutical composition containing the test material as an active ingredient for inhibiting and treating cancer. The pharmaceutical composition of the present invention, which contains, as an active ingredient, an inhibitor for inhibiting PAUF from binding with a binding partner, effectively inhibits PAUF signaling related to the onset of cancer, thus enabling various kinds of cancer (especially pancreatic cancer) to be treated.

13 Claims, 7 Drawing Sheets

(a)

(b)

US 10,023,915 B2

METHOD FOR SCREENING FOR A CANCER TREATMENT AGENT USING THE INTERACTION BETWEEN PAUF AND A BINDING PARTNER THEREOF

CROSS REFERENCE TO RELATED APPLICATIONS AND CLAIM OF PRIORITY

This patent application is a National Phase application under 35 U.S.C. § 371 of International Application No. PCT/KR2011/005684, filed Aug. 2, 2011, which claims priority to Korean Patent Application No. 10-2011-0027472 filed Mar. 28, 2011, entire contents of which are incorporated herein by reference.

Technical Field

The present invention relates to a method for screening a cancer treatment agent using an interaction between Pancreatic Adenocarcinoma Up-regulated Factor (PAUF) and its binding partner, and a pharmaceutical composition for cancer prevention or treatment.

Background Art

Pancreatic cancer is a deadly cancer that has a 5-year survival rate of 1~4% and a median survival period of approximately 5 months, and has an extremely poor prognosis as compared with other human cancers. Since approximately 90% of patients with pancreatic cancer cannot undergo radical operations when their cancers are found, the pancreatic cancer has an extremely poor prognosis in the human cancers. Moreover, its treatment has no choice but to depend on anti-cancer medication having a response rate of only about 20%, and thus development of its early diagnosis is very urgently needed as compared with other cancers occurring in the human body.

The present research team reported to the journal that Pancreatic Adenocarcinoma Up-regulated Factor (PAUF), as a preclinical candidate target gene that is induced from the human pancreatic and stomach cancers-specific gene group DNA chip database, is a novel gene associated with occurrence of pancreatic cancer (*Cancer Science*, 100(5):826-836 (2009)), and filed a patent application thereof (Korean Patent Registration No. 0954322).

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY

Although it was confirmed that carcinogenicity of pancreatic cancer cell lines is increased or reduced depending on induction or inhibition of a Pancreatic Adenocarcinoma Up-regulated Factor (PAUF) gene, PAUF protein signaling pathways have not yet been known. Intracellular or extracellular signaling is controlled by mutual bindings of several kinds of proteins. Therefore, the present inventors have tried to broaden the understanding of an anti-cancer mechanism targeting PAUF by finding proteins binding to PAUF and researching PAUF protein signaling pathways. As a result, the present inventors screened three proteins as a binding partner of PAUF, and established that new approaches for cancer treatment (particularly, pancreatic cancer) can be provided when the interactions between these proteins and PAUF are inhibited, so that the present invention was completed.

An aspect of the present invention is to provide a method for screening a cancer treatment agent.

Another aspect of the present invention is to provide a pharmaceutical composition for cancer prevention or treatment.

Still another aspect of the present invention is to provide a method for cancer prevention or treatment.

Other purposes and advantages of the present invention will become clarified by the following detailed description of invention, claims, and drawings.

In accordance with an aspect of the present invention, there is provided a method for screening a cancer treatment agent, the method including:

(a) contacting a test material with Pancreatic Adenocarcinoma Up-regulated Factor (PAUF) and its binding partner Glutaredoxin-3 (GLRX3), SNAP-associated protein (SNAPIN), or Ubiquitin-like 4A (UBL4A); and (b) analyzing whether or not the test material inhibits the binding of PAUF and its binding partner GLRX3, SNAPIN, or UBL4A to determine the test material to be a cancer treatment agent if the test material inhibits the binding.

Although it was confirmed that carcinogenicity of pancreatic cancer cell lines is increased or reduced depending on induction or inhibition of the PAUF gene, PAUF protein signaling pathways have not yet been known. Intracellular or extracellular signaling is controlled by mutual bindings of several kinds of proteins. Therefore, the present inventors tried to increase the understanding of an anti-cancer mechanism targeting PAUF by finding proteins binding to PAUF and researching PAUF protein signaling pathways. As a result, the present inventors screened three proteins as a binding partner of PAUF and established that new approaches for cancer treatment (particularly, pancreatic cancer) can be provided when the interactions between these proteins and the PAUF are inhibited.

According to the method of the present invention, the test material is contacted with PAUF and its binding partner GLRX3, SNAPIN, or UBL4A.

As used herein, the term "PAUF" refers to a protein which was first named by the present inventors (Korean Patent Registration No. 0954322). The above protein is differentially expressed in the pancreatic cancer tissue and the normal pancreatic tissue. Protein and nucleic acid sequences of PAUF are registered in GenBank (Accession number: EF067313). More preferably, the protein and nucleic acid sequences of PAUF has an amino acid sequence of SEQ ID NO: 1

As used herein, the term "GLRX3" refers to one of the glutaredoxin family group. Glutaredoxin is an oxidoreductase, and reduces various substrates by using glutathione as a cofactor. More preferably, GLRX3 has an amino acid sequence of SEQ ID NO: 2. The encoded protein inhibits apoptosis and takes a role in cell growth. Nucleic acid molecule expression of this protein serves as a cancer marker.

As used herein, the term "SNAPIN" refers to one of components of the Soluble NSF (N-ethylmaleimide Sensitive Fusion protein) Attachment protein REceptor (SNARE) complex, and a protein necessary for the binding and fusing of synaptic vesicles. More preferably, SNAPIN has an amino acid sequence of SEQ ID NO: 3. The phosphorylation state of the protein has been known to influence interactions between extracellular proteins, and cellular exocytosis of the synaptic vesicles.

As used herein, the term "UBL4A" refers to a protein encoded in human gene UBL4A, which has been known as a house keeping gene, but of which functions have not been known. However, it has been recently found that UBL4A is one component of the Bat3 complex needed in a transitional state for movement of synthetic proteins into the Endoplamic Reticulum (ER) membrane (*Nature*, 466(26):1120-1124 (2010)). More preferably, UBL4A has an amino acid sequence of SEQ ID NO: 4.

As proved in the following examples, PAUF is found to be bound with GLRX3, SNAPIN, or UBL4A in the cells, particularly, in the cancer cells.

Therefore, a test material determined to be in competition with PAUF in binding to GLRX3, SNAPIN, or UBL4A can inhibit the binding of PAUF and GLRX3, SNAPIN, or UBL4A by binding with PAUF, GLRX3, SNAPIN, or UBL4A.

The test material analyzed by the screening method of the present invention is a single compound, a mixture of compounds (e.g., a natural extract or a cell or tissue culture), an antibody, or a peptide. The test material may be obtained from synthetic or natural compound libraries. These compound libraries are obtained by methods known in the art. The synthetic compound libraries are commercially available from Maybridge Chemical Co. (UK), Brandon Associates (USA), Microsource (USA), and Sigma-Aldrich (USA), and the natural compound libraries are commercially available from Pan Laboratories (USA) and MycoSearch (USA).

The test material may be obtained from various combinational library methods known in the art, for example, from a biological library method, a spatially addressable parallel solid phase or solution phase library method, a synthetic library method requiring deconvolution, a "one-bead one-compound" library method, and a synthetic library method using affinity chromatography selection. The synthetic methods of molecular libraries are disclosed in DeWitt et al., *Proc. Natl. Acad. Sci. U.S.A.* 90: 6909 (1993); Erb et al. *Proc. Natl. Acad. Sci. U.S.A.* 91: 11422 (1994); Zuckermann et al., *J. Med. Chem.* 37: 2678 (1994); Cho et al., *Science* 261: 1303 (1993); Carell et al., *Angew. Chem. Int. Ed. Engl.* 33: 2059 (1994); Carell et al., *Angew. Chem. Int. Ed. Engl.* 33: 2061; and Gallop et al., *J. Med. Chem.* 37: 1233 (1994).

As used herein, the term "peptide" refers to a linear molecule in which amino acid residues bind to each other through peptide linkages, and usually includes 4~40 amino acid residues.

The peptide as a binding inhibitor inhibiting the binding between PAUF and the binding partner thereof is prepared by the solid-phase synthetic method conventionally employed in the art (Merrifield, R. B., *J. Am. Chem. Soc.* 85:2149-2154 (1963), Kaiser, E., Colescot, R. L., Bossinger, C. D., Cook, P. I., *Anal. Biochem.,* 34:595-598 (1970)). That is, an intermediate is obtained by allowing amino acids with protected α-amino and side chain functional groups to be immobilized on a resin, followed by removal of the α-amino protecting group, and then allowing remaining amino acids with protected α-amino and side chain functional groups to be sequentially coupled therewith in a desired sequence. The conventional methods were referred to for the amino acid sequence for producing the PAUF inhibitor peptide of the present invention (Chen L, Hahn H, Wu G, Chen C H, Liron T, Schechtman D, Cavallaro G, Banci L, Guo Y, Bolli R, Dorn G W, Mochly-Rosen D., *Proc. Natl. Acad. Sci.*, 98, 11114-9 (2001); Phillipson A, Peterman E E, Taormina P Jr, Harvey M, Brue R J, Atkinson N, Omiyi D, Chukwu U, Young L H., *Am. J. Physiol. Heart Circ. Physiol.,* 289, 898-907 (2005); and Wang J, Bright R, Mochly-Rosen D, Giffard R G., *Neuropharmacology.*, 47, 136-145 (2004)).

As used herein, the term "natural extract" refers to one that is extracted and obtained from various organs or parts of natural products (e.g., leaves, flowers, roots, stems, branches, peels, fruits, etc.). The natural extract may be obtained by using, as an extracting solvent, (a) water, (b) anhydrous or hydrous lower alcohols having 1 to 4 carbons (methanol, ethanol, propanol, butanol, n-propanol, iso-propanol, n-butanol, etc.), (c) a mixture solvent of lower alcohol and water, (d) acetone, (e) ethyl acetate, (f) chloroform, (g) 1,3-butyleneglycol, (h) hexane, and (i) diethylether.

Herein, an antibody may be used as the test material. The antibody specifically binds to PAUF, GLRX3, SNAPIN, or UBL4A. Alternatively, herein, the antibody used as a test material includes a bispecific antibody. For example, an antibody having bispecificity to PAUF and GLRX3 may be used. The antibody is a polyclonal or monoclonal antibody, and preferably a monoclonal antibody.

The antibodies may be produced by using the conventional methods known in the art, for example, a fusion method (Kohler and Milstein, *European Journal of Immunology*, 6:511-519 (1976)), a recombinant DNA method (U.S. Pat. No. 4,816,567), or a phage antibody library method (Clackson et al, *Nature*, 352:624-628 (1991) and Marks et al, *J. Mol. Biol.*, 222:58, 1-597 (1991)). General schemes for producing antibodies are described in detail in Harlow, E. and Lane, D., *Using Antibodies: A Laboratory Manual*, Cold Spring Harbor Press, New York, 1999; Zola, H., *Monoclonal Antibodies: A Manual of Techniques*, CRC Press, Inc., Boca Raton, Fla., 1984; and Coligan, *CURRENT PROTOCOLS IN IMMUNOLOGY*, Wiley/Greene, NY, 1991, which are incorporated by reference into the present specification. For example, hybridoma cells producing monoclonal antibodies may be obtained by fusing immortal cell lines into antibody-producing lymphocytes, and the technology therefor has been well known to those skilled in the art and can be easily performed. The polyclonal antibodies may be obtained by injecting antigens into an appropriate animal, collecting antisera from the animal, and then isolating antibodies from the antisera using the known affinity technique.

According to a preferred embodiment of the present invention, GLRX3, SNAPIN, or UBL4A may be contained in vitro. That is, the method of the present invention may be performed by using one reaction solution in vitro. For example, the analysis according to the present invention may be performed by using a reaction solution containing purified PAUF and GLRX3 proteins and the test material.

According to a preferred embodiment of the present invention, GLRX3, SNAPIN, or UBL4A may be contained in cells. That is, the method of the present invention may be performed by using an intracellular reaction. For example, it is analyzed whether or not the binding of PAUF and GLRX3 is inhibited in the cells by treating PAUF and GLRX3 expressing cells with the test material. According to a preferred embodiment of the present invention, cells used in the present invention are cancer cells. Since PAUF was overexpressed in cancer cells, the cancer cells provide an environment for facilitating the analysis according to the present invention. The used cancer cells include stomach cancer cells, lung cancer cells, breast cancer cells, ovarian cancer cells, liver cancer cells, bronchial cancer cells, nasopharyngeal carcinoma cells, laryngeal cancer cells, pancreatic cancer cells, bladder cancer cells, colon cancer cells, colorectal cells, cervical cancer cells, brain cancer cells, prostate cancer cells, bone cancer cells, various types of head and neck cancer cells, skin cancer cells, thyroid cancer cells, parathyroid cancer cells, and ureteral cancer cells, but are not limited thereto. More preferably, the cancer cells used in the present invention is a pancreatic cancer cells.

Herein, the protein identified as a binding partner of PAUF is GLRX3, SNAPIN, or UBL4A. Preferably, the binding partner of PAUF used in the method of the present invention is GLRX3. More preferably, the binding partner of PAUF used in the method of the present invention is characterized by being a thioredoxin domain of GLRX3. GLRX3 is composed of a N-terminal thioredoxin domain and two C-terminal glutaledoxin domains. As proved in the following examples, when a mutant (GLRX3C), of which the thioredoxin domain is removed, and a mutant (GLRX3N), of which two glutaredoxin domains are removed, are constructed, followed by in vivo co-immunoprecipitation assay, the structure (GLRX3N) composed of only the thioredoxin domain is co-immunoprecipitated with PAUF. On the other hand, the mutant, of which the thioredoxin domain is removed, is not co-immunoprecipitated with PAUF.

According to a preferred embodiment of the present invention, whether or not the test material inhibits the binding between PAUF and its binding partner is analyzed by contacting the test material with PAUF and its binding partner.

This binding assay may be performed through various methods known in the art. According to a preferred embodiment of the present invention, step (b) may be performed by a two-hybrid assay, a co-immunoprecipitation assay, a co-localization assay, a scintillation proximity assay (SPA), a UV or chemical cross-linking assay, a bimolecular interaction analysis (BIA), a mass spectrometry (MS) assay, a nuclear magnetic resonance (NMR) assay, or a fluorescence polarization assay (FPA).

As used herein, the term "two-hybrid assay" is based on module characteristics of the transcription factor composed of separable DNA-binding and -activating domains. In this case, GLRX3, SNAPIN, or UBL4A may be used as the bait, and PAUF may be used as a prey. Alternatively, a construction contrary to the above may be made. According to this method, an inhibiting material of the interaction between PAUF and GLRX3, SNAPIN, or UBL4A may be screened. The two-hybrid system simply uses two kinds of DNA constructs. For example, one construct allows the GLRX3-, SNAPIN-, or UBL4A-coding polynucleotide to be fused into the DNA binding domain-coding polynucleotide of the known transcription factor (e.g., GAL-4). The other construct allows the PAUF-coding DNA sequence to be fused into the activating domain-coding polynucleotide of the known transcription factor. If the bait and the prey interact with each other to form a complex in vivo, the DNA-binding and activating domains of the transcription factor are adjacent to each other, which triggers the transcription of a reporter gene (e.g., LacZ). If the test material inhibits the interaction between PAUF and GLRX3, SNAPIN, or UBL4A, the expression of the reporter gene may be prevented, and therefore, the test material can be used as a cancer inhibitor. Besides the two-hybrid assay, a three-hybrid assay may be performed in some cases (U.S. Pat. No. 5,283,317; Zervos et al., *Cell* 72, 223-232, 1993; Madura et al., *J. Biol. Chem.* 268, 12046-12054, 1993; Bartel et al., *BioTechniques* 14, 920-924, 1993; Iwabuchi et al., *Oncogene* 8, 1693-1696, 1993; and WO 94/10300).

According to the term "co-immunoprecipitation assay (Co-IP) ((Harlow and Lane, Eds., *Antibodies: A Laboratory Manual*, Cold Spring Harbor Laboratory (1988)), the antigenic material produced by culture cells can be measured even when its direct measurement is impossible due to its trace amount. First, $^3$H-lysine or the like is added in the culture solution to label a target material and then the culture supernatant is taken. When the same concentration of non-labeled target material that can form antigen-antibody complexes with specific antibodies is added to this supernatant to cause a precipitation reaction, the trace amount of labeled target material also undergoes the co-precipitation reaction together with precipitates, so that the target material can be measured by radioactive activity of the precipitates. An antibody targeting a known protein partially constituting a large protein complex is selected, and then the antibody is used to target the known protein to precipitate a total protein complex in a solution, so that an unknown protein of the complex is identified. That is, since the direct measurement of an unknown material is impossible due to its trace amount, a target material is labeled in a culture liquid, followed by taking a culture supernatant, and then the same concentration of non-labeled target material that can form protein complexes together with specific antibodies is added to the supernatant to cause a precipitation reaction, with the result that the trace amount of labeled target material also undergoes a co-precipitation reaction. This concept of pulling protein complexes out of solution is sometimes referred to as a "pull-down". The co-immunoprecipitation assay is widely used to analyze protein-protein interactions.

As used herein, the term "co-localization assay" refers to a type of technology that the fluorescence microscopy is used to observe the spatial overlap between two (or more) different fluorescent labels, each having a separate emission wavelength, to see if the different "targets" are located in the same area of the cell or very near to one another. Proteins stained with two different fluorescent materials are scanned by a confocal microscope, and colors shown at specific locations are measured. Here, it may be established that two kinds of proteins are present at one location, and thus it may be inferred that these proteins interact with each other, that is, functionally bind to each other (Manders et al, *Journal of Microscopy* 169:375-382 (1993); Pawley J B, *Handbook of Biological Confocal Microscopy*, (2006)).

As used herein, the term "scintillation proximity assay (SPA)" refers to a type of technology that antibodies are attached to polyvinyl-toluene plastic scintillator beads which induce fluorescence due to electrons having energy and then antigens selectively binding to the antibodies attached to the beads are labeled with radionuclides emitting low-energy electrons, of which energy is easily lost or dissipated in an aqueous solution, so that the degree of antigen-antibody binding is measured through fluorescent measurement (Alouani, Methods *Mol. Biol.* 138:135-41 (2000)). This assay can overcome difficulty in construction of general systems, caused by the need of a separating procedure of binding fractions and free fractions, which is a disadvantage of the general radioimmunoassay, and can provide high sensitivity and skip the separating procedure. When the antigens labeled with radionuclides bind to the antibodies attached onto the beads, the low-energy electrons emitted from the radionuclides labeling the antigens reach the beads to transfer energy thereto, and the beads receiving the energy emit fluorescence. The emitted fluorescence can be measured by a liquid scintillation counter, and here the emitted fluorescence is increased in proportion to the antibody-antigen binding amount.

As used herein, the term "chemical cross-linking assay" refers to a type of technology that is used in analyzing small unit structures of proteins or functional characteristics exhibited by intermolecular reactions, such as protein-nucleic acid interactions and protein-protein interactions, by applying a cross-linking reagent to biopolymers, such as proteins or nucleic acids, to form chemical covalent linkages (Fancy, *Curr. Opin. Chem. Biol.* 4:28-33 (2000)). In addition, the chemical cross-linking assay is used in immobilization of protein molecules and stabilization in protein conjugate structures by a covalent linkage, such as labeling antibodies with enzymes. As the cross-linking agent, a bivalent cross-linking agent having functional groups at both ends thereof may be used, and here, the functional groups specifically react with functional groups, such as an amine group ($-NH_2$), a thiol group ($-SH$), and a carboxyl group ($-COOH$), in the same molecule thereof, or are activated by radiation of light. The binding force between proteins is too weak or temporary to observe interactions between proteins, but the use of chemical cross-linking assay facilitates capturing and analyzing the mutual binding between the proteins.

As used herein, the term "bimolecular interaction analysis (BIA)" refers to a type of technology of analyzing a specific interaction in real time, and this analysis may be performed without labeling of interactants (e.g., BIAcore™) (Sjolander & Urbaniczky, *Anal. Chem.* 63:2338-2345 (1991), and Szabo et al., *Curr. Opin. Struct. Biol.* 5:699-705 (1995)). The change in Surface Plasmon Resonance (SPR) may be used as an indicator for the real-time reaction between molecules.

As used herein, the term "fluorescence polarization assay (FPA)" refers to a type of technology that a body fluid (particularly, blood) containing a C-reactive protein (CRP), as a subject to be measured, is added into a mixture solution of a tracer having a CRP bound with flourescein as a fluorescent pigment, and an antibody specifically binding to the CRP, and the CRP is measured based on the competition between the tracer and the CRP with respect to the antibody in the mixture solution (Degterev, et al., *Nature Cell Biology* 3:173-182 (2001)).

The Mass spectrometry (MS) assay (McLafferty et al., *Science* 284:1289-1290 (1999) and Degterev, et al., Nature Cell Biology 3:173-182 (2001)) or the nuclear magnetic resonance (NMR) assay is used to analyze structures of unknown samples.

According to a preferred embodiment of the present invention, the cancer treatment agent screened by the present invention may be used to treat various cancers. Preferably, the cancer treatment agent screened by the present invention may be used to treat stomach cancer, lung cancer, breast cancer, ovarian cancer, liver cancer, bronchial cancer, nasopharyngeal carcinoma, laryngeal cancer, pancreatic cancer, bladder cancer, colon cancer, colorectal cancer, cervical cancer, brain cancer, prostate cancer, bone cancer, head and neck cancer, skin cancer, thyroid cancer, parathyroid cancer, or ureteral cancer, and more preferably pancreatic cancer.

Herein, since PAUF is highly expressed particularly in the pancreatic cancer cells, the binding amount of PAUF and its binding partner GLRX3, SNAPIN, or UBL4A is high. Therefore, the test material may be determined to be a cancer treatment agent if the test material inhibits the binding of PAUF and its binding partner GLRX3, SNAPIN, or UBL4A.

According to another aspect of the present invention, the present invention provides a pharmaceutical composition for cancer prevention or treatment, the composition including, as an active ingredient, a material inhibiting the binding of PAUF and its binding partner GLRX3, SNAPIN, or UBL4A.

According to still another aspect of the present invention, the present invention provides a method for cancer prevention or treatment, the method including administering a pharmaceutical composition to a subject in need thereof, the pharmaceutical composition including, as an active ingredient, a material inhibiting the binding of PAUF and its binding partner GLRX3, SNAPIN, or UBL4A.

Since the pharmaceutical composition of the present invention includes, as an active ingredient, a material inhibiting the binding of PAUF and its binding partner GLRX3, SNAPIN, or UBL4A, overlapping descriptions between the pharmaceutical composition and the method for cancer prevention or treatment will be omitted in order to avoid excessive complexity of the present specification.

In the case where the composition of the present invention is a pharmaceutical composition, the composition of the present invention includes: (i) an effective amount of a binding inhibitor inhibiting the binding between PAUF and its binding partner GLRX3, SNAPIN, or UBL4A; and (ii) a pharmaceutically acceptable carrier. As used herein, the term "effective amount" refers to a dosage sufficient to exhibit the treatment efficacy of the present invention described above.

The pharmaceutically acceptable carrier contained in the pharmaceutical composition of the present invention is typically used at the time of pharmaceutical preparation, and includes carbohydrate-based compounds (e.g., lactose, amylose, dextrose, sucrose, sorbitol, mannitol, starch, cellulose, etc.), acacia gum, calcium phosphate, alginate, gelatin, calcium silicate, microcrystalline cellulose, polyvinylpyrrolidone, cellulose, water, syrup, a salt solution, alcohol, Arabic gum, vegetable oils (e.g., corn oil, cotton seed oil, soybean oil, olive oil, coconut oil, etc.), polyethylene glyco61, methyl cellulose, methylhydroxy benzoate, propylhydroxy benzoate, talc, magnesium stearate, and mineral oils, but is not limited thereto. The pharmaceutical composition of the present invention may further include, besides the above components, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be orally or parenterally administered. In the case of parenteral administration, intravenous injection, subcutaneous injection, muscle injection, or the like may be employed.

The appropriate dosage of the pharmaceutical composition of the present invention is varied depending on factors, such as the method of formulation, the manner of administration, the age, body weight, sex, morbidity, and diet of the patient, the time of administration, the route of administration, the rate of excretion, and response sensitivity. The ordinarily skilled practitioner can easily determine and prescribe the dosage effective for desired treatment or prevention. According to a preferred embodiment of the present invention, the appropriate dosage per day is 0.0001~100 mg/kg (body weight). The dosage may be administered once a day or divided into multiple doses.

The pharmaceutical composition of the present invention may be formulated into a unit dosage form or may be formulated by being contained in a multi-dose container, using a pharmaceutically acceptable carrier and/or excipient, according to the method easily performed by person having ordinary skills in the art to which the present invention pertains. Here, the dosage form may be a solution in an oily or aqueous medium, a suspension, or an emulsion, or an extract, a powder, a granule, a tablet, or a capsule, and may further include a dispersant or a stabilizer.

In the pharmaceutical composition of the present invention, the binding inhibitor between PAUF and the binding partner thereof, which is used as an active ingredient, may be one of various materials. For example, the active ingredient includes a single compound, a mixture of compounds (e.g., a natural extract or a cell or tissue culture), an antibody, or a peptide.

The active ingredient used in the present invention can inhibit the binding between PAUF and the binding partner thereof and thus effectively block signaling of PAUF associated with cancer incidence, thereby treating various cancers (particularly, a pancreatic cancer).

Features and advantages of the present invention are summarized as follows:

(a) According to the present invention, the cancer treatment agent is screened by analyzing whether or not the test material inhibits the binding of PAUF and its binding partner GLRX3, SNAPIN, or UBL4A.

(b) The pharmaceutical composition of the present invention including, as an active ingredient, a binding inhibitor between PAUF and its binding partner, can effectively block signaling of PAUF associated with cancer incidence, thereby treating various cancers (particularly, a pancreatic cancer).

BRIEF DESCRIPTION OF THE DRAWINGS

FIG. 5(a) is a gel image showing expression of GLRX3 mRNA in human pancreatic cancer cell lines, and FIG. 5(b) is a gel image showing expression of GLRX3 protein in human pancreatic cancer cell lines.

DETAILED DESCRIPTION

Figure 1:
FIG. 1 is an image showing PAUF-binding protein candidates grown in a medium containing X-gal and excluding adenine, histidine, leucin, and tryptophane, which were obtained from results of yeast two-hybrid assay in HeLa cell cDNA library.

Hereinafter, the present invention will be described in detail with reference to examples. These examples are only for illustrating the present invention more specifically, and it will be apparent to those skilled in the art that the scope of the present invention is not limited by these examples.

EXAMPLE

Materials and Methods
Cell Incubation

Eight pancreatic cancer cell lines (AsPC-1, BxPC-3, Capan-1, Capan-2, CFPAC-1, HPAC, MIAPaCa-2, and PANC-1), cervical cancer cell lines (HeLa), and Chinese hamster ovary (CHO) cell lines were purchased from American Type Culture Collection (ATCC; Manassas, Va., USA). The CHO/PAUF cell line was constructed by transfecting of the pcDNA3.1(+)-PAUF-Myc/H is plasmid into the CHO cells (Sun A. Kim, et al., *Cancer Sci.* 100(5):828-836 (2009)). All cells were incubated in conditions of 5% $CO_2$ and 37.

Plasmid Construction

For yeast two-hybrid analysis, the pGBKT7-PAUF plasmid was constructed as a pray protein by inserting the PAUF expression sequence into the pGBKT7 vector (Clontech), using NcoI and EcoRI restriction enzymes. For mammalian expression, the PAUF gene was inserted into the pcDNA3.1 (+)-Myc/His vector (Invitrogen), producing the pcDNA3.1 (+)-PAUF-Myc/His plasmid (Sun A. Kim, et al., *Cancer Sci.* 100(5):828-836 (2009)). For expression of GLRX3 (H14) and its deficient mutants (GLRX3N and GLRX3C), protein coding sequence amplification was performed by using the yeast plasmid pGADT7Rec-H14 (clontech) containing H14, as a template, and respective primers (table 1), and then inserted into the 3×FLAG-CMV14 vectors (Sigma) by using the NotI and BamHI sites. H13 (SNAPIN) and H32 (UBL4A) protein coding sequences were amplified by using the primers of table 1 (using pGADT7Rec-H13 and pGADT7 Rec-H32 as a template), and then were inserted into the 3×FLAG-CMV14 vectors by using the HindIII and BamHI sites. All the constructed plasmids were confirmed by sequencing.

TABLE 1

| construct | Primer Sequence (Forward/Reverse) | |
|---|---|---|
| pGBKT7-PAUF | 5'-CCCGCCATGGCGATGTGGAGGGTGCC-3' | (SEQ ID NO: 5) |
| | 5'-GCCCGAATTCGCGACCCACGGGTGAGT-3' | (SEQ ID NO: 6) |
| 3xFLAG-CMV14/H13 (SNAPIN) | 5'-CCCAAGCTTGGGATGGCGGGGGCTGGTTCC-3' | (SEQ ID NO: 7) |
| | 5'-CGCGGATCCGCGTTTGCCTGGGGAGCCAGGG-3' | (SEQ ID NO: 8) |
| 3xFLAG-CMV14/H14 (GLRX3) | 5'-AATGCGGCCGCAGCATGGCGGCGGGGGC-3' | (SEQ ID NO: 9) |
| | 5'-CGCGGATCCGCGATTTTCTCCTCTCAGTATAGGCAGC-3' | (SEQ ID NO: 10) |
| 3xFLAG-CMV14/H14N (GLRX3N) | 5'-AATGCGGCCGCAGCATGGCGGCGGGGGC-3' | (SEQ ID NO: 11) |
| | 5'-CGCGGATCCGCAGGGGGCAGCATGAGTCAATT-3' | (SEQ ID NO: 12) |

TABLE 1-continued

| construct | Primer Sequence (Forward/Reverse) | |
|---|---|---|
| 3xFLAG-CMV14/H14C (GLRX3C) | 5'-AATGCGGCCGCATGAACCTTCGCTTGAAGAAATTGACTC-3'<br>5'-CGCGGATCCGCGATTTTCTCCTCTCAGTATAGGCAGC-3' | (SEQ ID NO: 13)<br>(SEQ ID NO: 14) |
| 3xFLAG-CMV14/H32 (UBL4A) | 5'-CCCAAGCTTGGGATGCAGCTGACGGTGAAA-3'<br>5'-CGCGGATCCGCGTTTGGAGAAGCCCTTCTCCA-3' | (SEQ ID NO: 15)<br>(SEQ ID NO: 16) |

Yeast-Two-Hybrid Screening

Yeast two-hybrid screening was performed by using the MATCHMAKER two-hybrid system (Clontech). The yeast strain AH109 was transfected with the prey plasmid pGBKT7-PAUF, and the transfected AH109 was hybridized with the previously transfected HeLa cell cDNA library (Clontech). The hybridized yeast cells were grown in minimal selective media (QDO plates) excluding adenine, histidine, leucin, and tryptophan, followed by first selection. Tentative positive clones were selected from those exhibiting LacZ activity in the β-galatosidase test. The plasmids were extracted from the finally selected forty-one positive clones, and then introduced into bacteria, followed by expansion culture. The plasmids taken from the bacteria were sequenced, and matched sequences were searched by the BLAST program.

In Vitro Binding Experiment (His Pull-Down)

For His pull-down experiment, the concentrated culture medium of CHO/PAUF-His cell was reacted with Ni-NTA resin in the Ni-NTA binding buffer with 10 mM imidazole at 4° C. for overnight. The Ni-NTA resin incubated overnight was washed three times with the Ni-NTA binding buffer containing 20 mM imidazole, and then reacted with 800 μg total proteins from CFPAC-1 for 4 hours. After 4 hours, the resin was washed five times with the Ni-NTA binding buffer, and the proteins bound to the resin were dissolved in the SDS sample buffer, followed by Sodium Dodecyl Sulfate-Polycrylamide Gel Electrophoresis (SDS-PAGE) analysis and then western blotting.

In Vivo Binding Experiment

Appropriate plasmid combination was transfected into HeLa cells using Lipofectamine Plus (Invitrogen). At 48 hours post-transfection, transfected cells were dissolved in the cell lysis buffer (10 mM Tris, pH 7.5, 10 mM NaCl, 2 mM EDTA, 0.5% TRITON X-100 (4-(1,1,3,3-tetramethyl-butyl)phenyl-polyethylene glycol), 1 mM PMSF, and protease inhibitor cocktail (Roche Diagnostics, Mannheim, Germany)) to obtain total proteins. For secretary protein preparation, the culture medium was exchanged with a serum-free culture medium at 24 hours post transfection of the plasmid, followed by culturing again for 24 hours, and then the culture medium was collected. The collected culture medium was centrifuged to discard cell components. For immunoprecipitation of His-tagged proteins, 300 μg of total proteins and the culture medium were reacted with the Ni-NTA resin at 4° C. for 5 hours. After 5 hours, the reacted material was washed five times with a washing buffer (50 mM Tris, pH 7.5, 150 mM NaCl, and 0.5% TRITON X-100), and then proteins attached to the resin were dissolved in the SDS sample buffer, followed by SDS-PAGE and then western blotting.

Protein Extraction and Western Blot Analysis

Cellular total proteins were extracted in lysis buffer (50 mM Tris, 150 mM NaCl, 25 mM β-glycerophosphate, 25 mM NaF, 0.5 M EDTA, 1% NP-40, 0.1 mM PMSF, and 1% protease inhibitor cocktail (Roche)). For secretary protein preparation, the cell culture medium incubated under serum-free conditions was centrifuged to discard cell components, and then concentrated by using microcon centrifugal filters (10 kDa cutoff; Amicon, Houston, Tex.). The cellular total proteins and culture medium were separated by SDS-PAGE, and then transferred to the PVDF membrane (Millipore, Billerica, Mass.). The membranes were blocked in 5% (w/v) non-fat dry milk, and probed with either the anti-His antibody (1:1000; Santa Cruz Biotechnology, Santa Cruz, Calif., USA) or anti-PAUF antibodies ((Cancer Science, 100(5): 826-836 (2009)). The immunoreactive proteins were visualized using the West Pico Chemiluminescent Substrate (Thermo Scientici, Rockford, Ill.).

Reverse Transcription-Polymerase Chain Reaction (RT-PCR)

RT-PCR was performed to expression of GLRX3 mRNA of pancreatic cancer cell lines. The PCR conditions were 95° C. for 30 seconds, 55° C. for 30 seconds, and 72° C. for 30 seconds for a total of 28 cycles. Primers for PCR were as follows: GLRX3 forward primer, 5'-GGGCGGCTGAG-GCAGCT-3' (SEQ ID NO: 17); GLRX3 reverse primer, 5'-GCAGGGGGCAGCATGAGTC-3' (SEQ ID NO: 18); ACTB forward primer, 5'-ggcatcctcaccctgaagta-3' (SEQ ID NO: 19); and ACTB reverse primer, 5'-ggggtgttgaaggtct-caaa-3' (SEQ ID NO: 20).

Immunohistochemical Staining

Pancreatic cancer tissues and adjacent non-cancer tissues were obtained by surgical resection. Paraformaldehyde-fixed, paraffin-embedded tissue sections were deparaffinized in xylene and rehydrated in a graded ethanol series. Endogenous peroxidase activity was blocked in 0.3% (v/v) hydrogen peroxide. Microwave antigen retrieval was performed in citrate buffer (0.01M, pH 6.0) for 3 minutes. To prevent non-specific staining, the sections were preincubated with 10% normal donkey serum. The blocked sections were then incubated with monoclonal antibody (1:500, Abnova, Taipai, Taiwan) against GLRX3, followed by incubation with biotinylated Link Universal and streptavidin-horseradish peroxidase (HRP) conjugate (DakoCytomation, Ft. Collins, Colo., USA). the section were stained with chromogen and counterstained with Harris hematoxylin solution (Sigma-Aldrich).

Experiment Results

Identification of PAUF-Binding Protein; Selection of Three PAUF-Binding Protein Candidates Through HeLa Cell Library Screening 41 clones binding to the PAUF protein were found by the yeast two-hybrid method in the human HeLa cell cDNA library (FIG. 1), and the respective clones were identified through DNA sequencing (Tables 2 and 3).

Of these, H13 (SNAPIN), H14 (GLRX3), and H32 (UBL4A) proteins having high x-gal activity were subjected to additional experiments for PAUF binding.

TABLE 2

Clone # 14, 13, 12, 32: x-gal activity

| Clone # | Identified protein |
|---|---|
| 2/36 | *Homo sapiens* eukaryotic translation initiation factor 3, subunit 5 epsilon, 47 kDa (EIF3S5) |
| 21 | *Homo sapiens* eukaryotic translation initiation factor 3, subunit 8 110 kDa (EIF3S8) |
| 14 | *Homo sapiens* thioredoxin-like 2, mRNA (cDNA clone MGC: 12349 IMAGE: 3686411, complete cds Length = 1275 |
| 13 | *Homo sapiens* SNAP-associated protein, mRNA (cDNA clone MGC: 2717 IMAGE: 2821705, complete cds Length = 1008 |
| 15/25 | PREDICTED: *Pan troglodytes* similar to Sorcin (22 kDa protein) (CP-22) (V19) (LOC463518) |
| 17 | *Homo sapiens* SNF8, ESCRT-II complex subunit, homolog (*S. cerevisiae*), mRNA (cDNA clone MGC: 47686 IMAGE: 3900806)/EAP30 subunit of ELL complex |
| 12 | *Homo sapiens* diaphanous homolog 1 (*Drosophila*) (DIAPH1), mRNA Length = 5662 |
| 38 | *Homo sapiens* actinin, alpha 4 (ACTN4), mRNA Length = 3893 |
| 31 | *Homo sapiens* integrator complex subunit 1 (INTS1) |
| 18 | *Homo sapiens* mediator complex subunit 12 (MED12) |
| 5 | *Homo sapiens* mesothelin, transcript variant 1 |
| 11 | *Homo sapiens* ribosomal protein, large, P2(RPLP2) |
| 34 | P68 RNA replicase |
| 37 | *Homo sapiens* dicarbonyl/L-xylulose reductase (DCXR) |
| 41/39 | *Homo sapiens* prosaposin (PSAP), transcript variant 3 |
| 4 | *Homo sapiens* estrogen-related receptor alpha (ESRRA) |

TABLE 3

| Clone # | Identified protein |
|---|---|
| 16/20/29 | Human RNA for HLA-Bw72 antigen |
| 30 | *Homo sapiens* (clone pMF18) MHC class I HLA-Bw62 |
| 27 | HLA-C major histocompatibility complex, class I, C |
| 32 | *Homo sapiens* Ubiquitin-like 4A |
| 10 | *Homo sapiens* TruB pseudouridine (psi) synthase homolog 1 (*E. coli*) (TRUB1) |
| 33 | *Homo sapiens* ribosomal protein S28 |
| 19 | *Homo sapiens* peroxiredoxin 5 (PRDX5), nuclear gene encoding mitochondrial protein, transcript variant 3 |
| 22 | *Homo sapiens* valyl-tRNA synthetase (VARS) |
| 23 | *Homo sapiens* required for meiotic nuclear division 5 homolog B (*S. cerevisiae*) (RMND5B) |
| 28 | *Homo sapiens* dehydrogenase/reductase (SDR family) member 10 (DHRS10) |
| 1 | *Homo sapiens* hypoxanthine phosphoriboxyltransferase 1 (Lesch-Nyhan syndrome) (HPRT1) |
| 3 | *Homo sapiens* chromosome 19 clone LLNL-FOS_33C4, complete sequence Length = 22624/*Homo sapiens* chromosome 19 genomic contig. Alternate assembly (based on HuRef SCAF_1103279181064)Length = 3790315 Features in this part of subject sequence: protease, serine-like 1 |
| 7/40 | *Homo sapiens* ferritin, light polypeptide |
| 26/35 | *Homo sapiens* BAC clone RP11-753F4 from 2 |
| 6/24 | *Homo sapiens* BAC clone RP11-762N20 from 2 |
| 8/9 | *Homo sapiens* ACN9 homolg (*S. cerevisie*) |

In Vitro Binding Experiment

Figure 2:
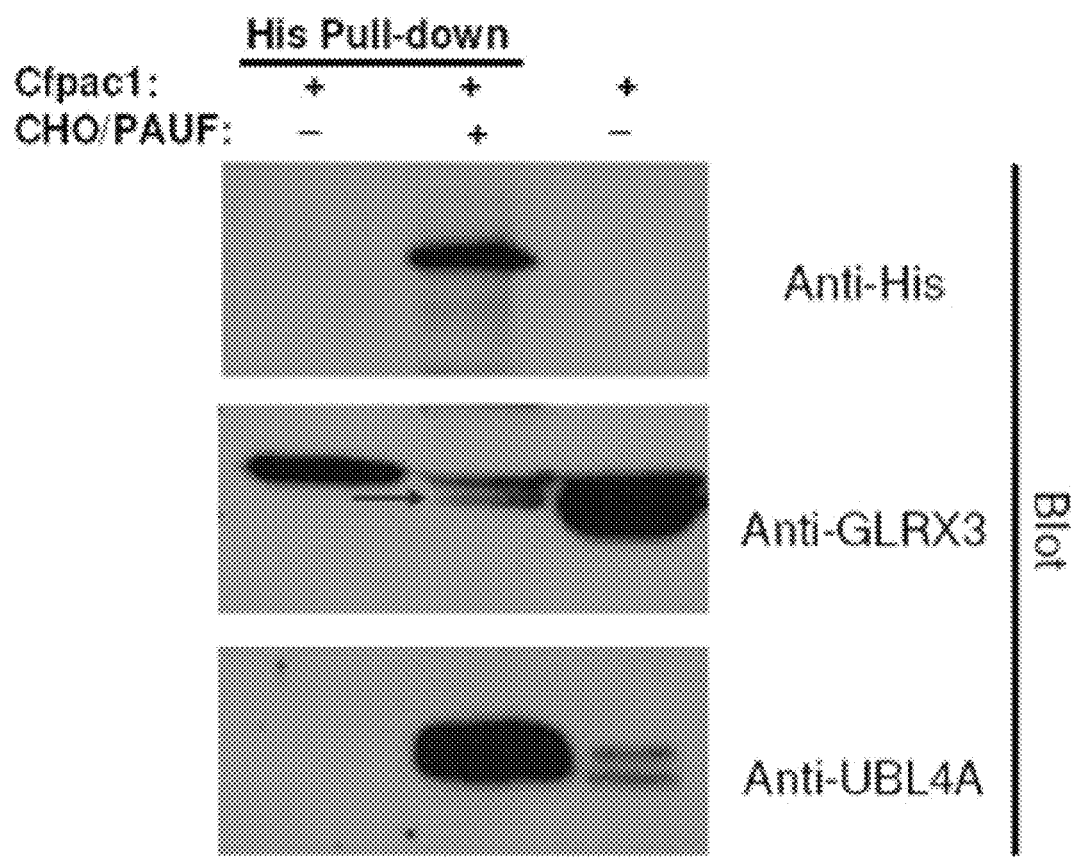
FIG. 2 is a gel image illustrating pull-down results of GLRX3 and UBL4A in cell extracts of the pancreatic cancer cell line CFPAC-1 using the His-PAUF protein as a pray. The gel image was obtained when the His-PAUF was immobilized on the Ni-NTA resin, followed by reaction with CFPAC-1 protein extracts, extraction of proteins immunoprecipitated together with the Ni-NTA resin, separation using SDS-PAGE, and then western blotting using anti-HIS, anti-GLRX3, and anti-UBL4A antibodies.

Only the PAUF-His protein from the PAUF overexpressing CHO/PAUF cells was bound to the Ni-NTA resin (PAUF-His/Ni-NTA), which was then induced to bind to total proteins from the pancreatic cancer cell line CFPAC-1. It was confirmed that the GLRX3 protein and the UBL4A protein were bound to the PAUF-binding Ni-NTA resin, respectively, but were not bound to the Ni-NTA resin itself without PAUF binding thereto (FIG. 2). This results show that the binding between PAUF and GLRX3 or UBL4A is specific.

In Vivo Binding Experiment; Co-Immunoprecipitation Assay

Figure 3:
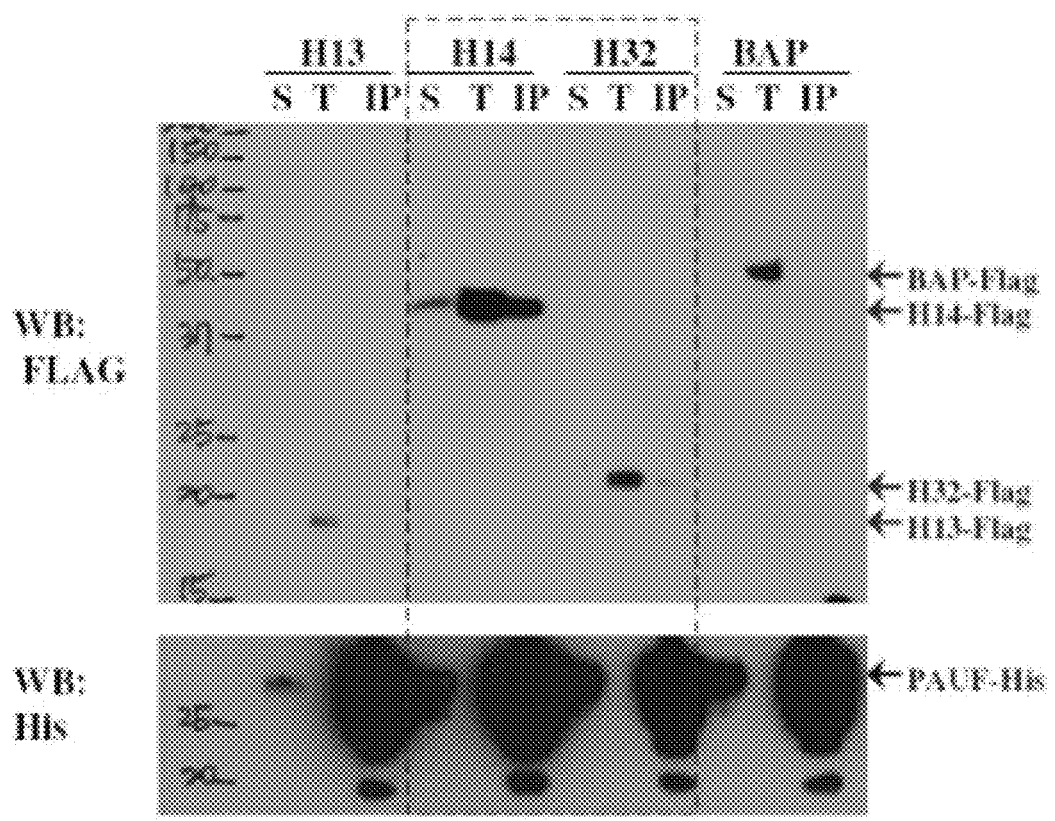
FIG. 3 is an in vivo experiment gel image obtained when plasmides respectively expressing H13-, H14-, and H32-FLAG and a His-PAUF expressing plasmid were co-expressed in HeLa cell line, followed by reacion of cell protein extracts with the Ni-NTA resin to separate binding precipitates, and then western blotting on the separated binding precipitates.

Since the pull-down assay shows the binding between proteins derived from different cells, the binding may be differentiated from the in vivo binding. In order to overcome this drawback, genes coding respective proteins, PAUF, GLRX3, and UBL4A, were inserted into vectors, which were then transfected into HeLa cells, followed by co-immunoprecipitation, so that the binding between proteins was confirmed while the respective proteins were expressed in the cells. As a result, the binding between two proteins were confirmed in PAUF/GLRX3-expressing cells and PAUF/UBL4A-expressing cells (FIG. 3). On the other hand, the binding between PAUF and Bacterial Alkaline Phasphatase (BAP) was not shown in PAUF/BAP-introduced cells, as a control.

N-Terminal Domain of GLRX3 is Included in the Binding with PAUF

Figure 4:
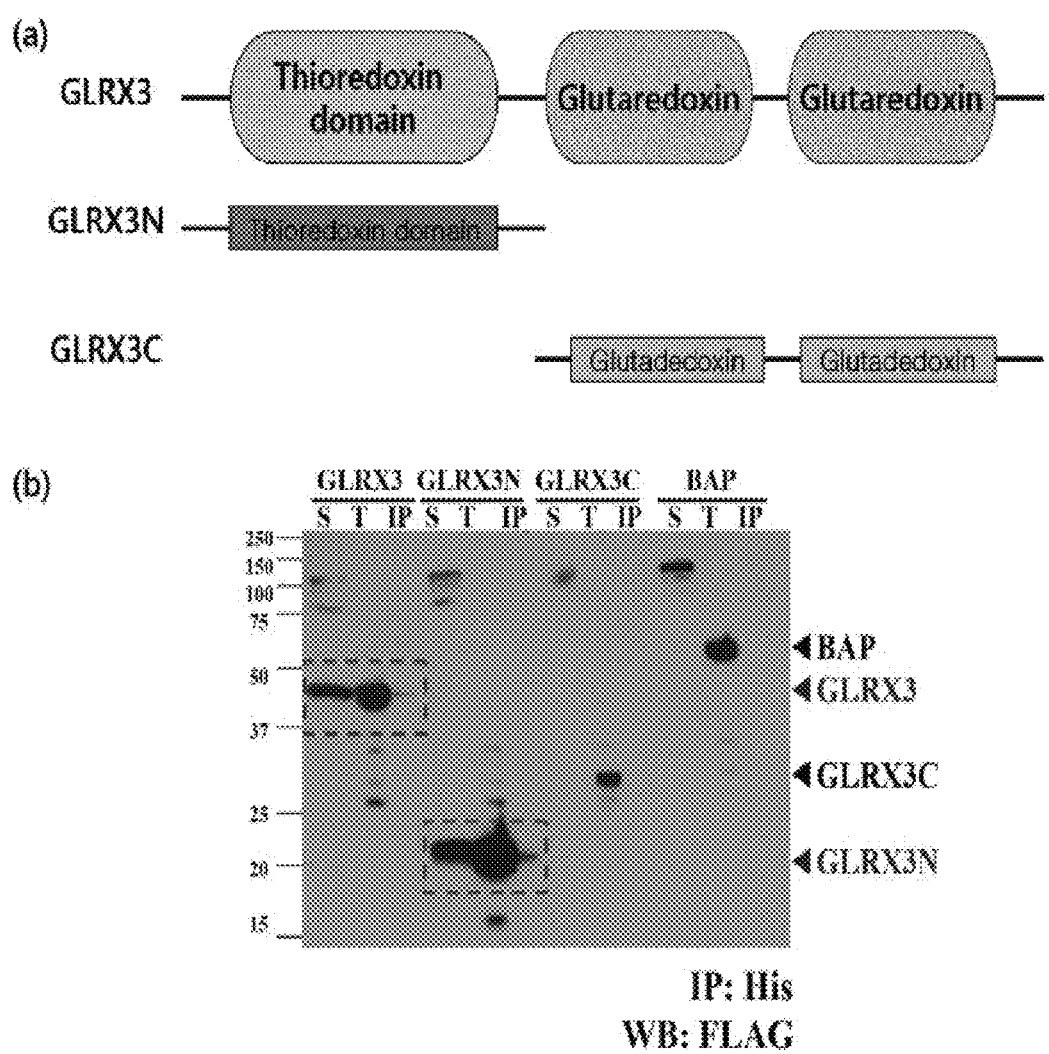
FIG. 4(a) shows mutant structures of GLRX3 for PAUF-binding domains of GLRX3.
FIG. 4(b) illustrates an in vivo binding experiment between the GLRX3 mutants and PAUF.

The GLRX3 protein, which is one of the PAUF-binding proteins, is composed of an N-terminal thioredoxin domain and two C-terminal glutaredoxin domains ((a) of FIG. 4). In order to validate which one of the two domains binds to PAUF, two types of GLRX3 mutant structures (GLRX3N and GLRX3C) were established as shown below in (a) of FIG. 4 to perform an in vivo co-immunoprecipitation experiment. As a result, GLRX3 and the structure (GLRX3N) composed of only the thioredoxin domain of the GLRX3 were co-immunoprecipiated with PAUF, but the structure (GLRX3C) composed of only the C-terminal domains of GLRX3 was not co-immunoprecipitated with PAUF. These results show that the N-terminal thioredoxin domain of the GLRX3 binds to PAUF ((b) of FIG. 4).

Figure 5:
FIG. 5 shows the expressions of mRNA and protein of GLRX3.
Figure 5:
Figure 5:
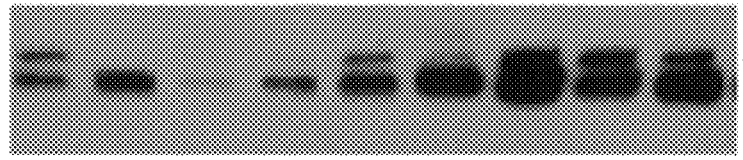
Figure 5:
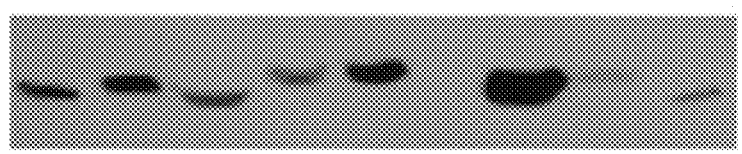
Figure 5:
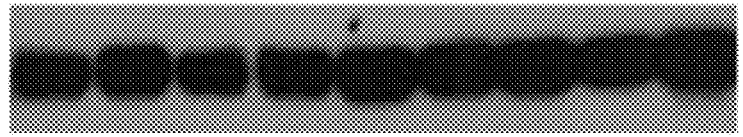
Figure 6:
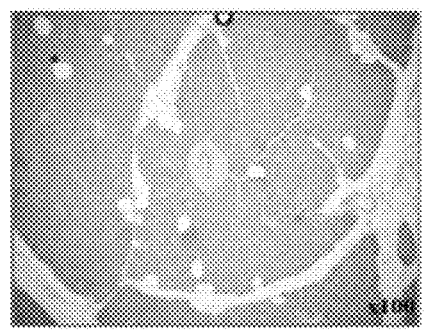
FIG. 6 shows images validating expressions of GLRX3 protein in the pancreatic cancer patient tissues by an immunohistochemical staining. The upper microscopic images show normal pancreatic tissues and lower microscopic images show pancreatic cancer tissues.
Figure 6:
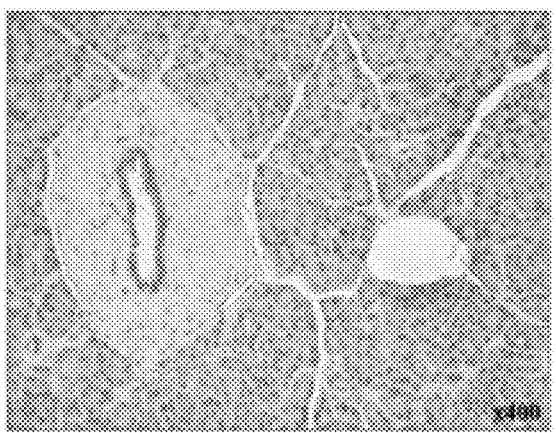
Figure 6:
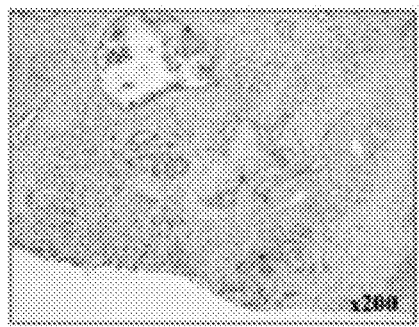
Figure 6:
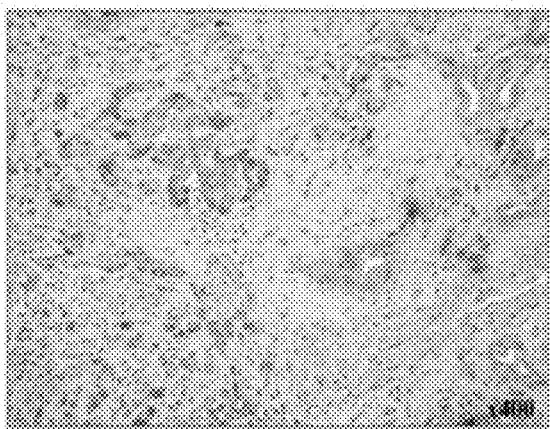

GLRX3 Expression Distribution in Pancreatic Cancer Cell Lines and Patient Tissues As the result of confirming the degree of GLRX3 mRNA expression in the pancreatic cancer cell lines, non-neoplastic human pancreatic duct epithelial (HPDE) cell line, and cervical cancer cell line (HeLa), it was confirmed that the GLRX3 mRNA was expressed in all the pancreatic cancer cell lines and HeLa cells, but slightly expressed in the non-neoplastic human pancreatic duct cell line (HPDE) ((a) of FIG. 5). It was confirmed that the GLRX3 protein was expressed in almost pancreatic cancer cells and normal pancreatic duct cells, and the GLRX3 protein was secreted in vitro ((b) of FIG. 5). In addition, it was confirmed that, through immunohistochemical-staining in the patient tissues, the GLRX3 protein was expressed more in the cytoplasm of the pancreatic cancer tissues than the normal tissues (FIG. 6).

Discussion

GLRX3 has been known to be involved in immune-related signaling, but since GLRX3 is an enzyme having no sequences necessary for activation, it is expected that GLRX3 is functionally operated by proteins binding thereto. It has been reported that the expression of GLRX3 is increased in the human colorectal cancer and lung cancer (Cancer Epidemiology 2009, Proteomics 2008). In addition, it has been reported that the inhibition of GLRX3 expression induces an increase in the level of reactive oxygen species (ROS) and an inhibition in NF-kB activity, thereby inhibiting cell proliferation, in the breast cancer cell lines. In addition, it has been reported that the GLRX3 mRNA levels is closely associated with metastasis and the survival rate of breast cancer patients (Journal of clinical investigation, 2010). However, the mechanism that GLRX3 inhibits the ROS has not been accurately known.

Intracellular byproducts, such as oxygen molecules or ROS, form a bisulfide linkage between intracellular proteins, and this structure influences stability of proteins. Two main paths for reducing this disulfide linkage in vivo are thioredoxin and glutaredoxin paths. It is recently reported that GLRX3 is a detoxification-related enzyme.

Cancer cells have higher metabolic activity than normal cells, and thus the ROS level thereof is increased. In addition, many cancer cells have a relatively enhanced antioxidant defense mechanism in order to maintain the oxidation-reduction state and suppress apoptosis. This phenomenon may help the cancer cells have more malignant actions and drug resistances.

To sum up, the binding of PAUF and GLRX3 which were overexpressed in cancer cells are expected to participate to removal of ROS.

The UBL4A protein having unknown functions has been simply known as a house keeping gene, but it was recently found that the UBL4A protein is one component of the Bat3 complex needed in a transitional state for movement of synthetic proteins into the Endoplamic Reticulum (ER) membrane (Nature, 466(26):1120-1124 (2010)).

Figure 7:
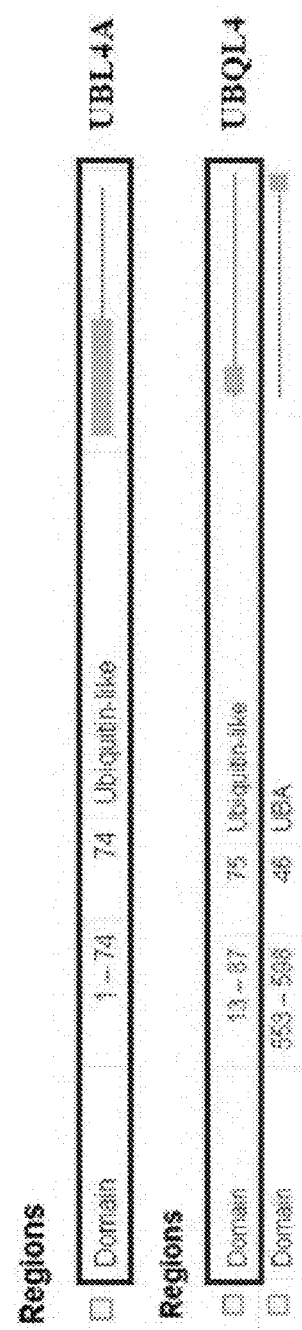
FIG. 7 illustrates peptide sequences of UBL4A and UBQL4 proteins by using the PAUF protein.

Before the functions of PAUF were known, it was reported that Zymogen Granule protein 16 monolog B (ZG16B), which is one of the other names of PAUF, and a protein called UBQLN4 (Ubiquilin-4) interact with each other (Cell, 125(4):801-14 (2006)). This report indicated that the binding site between UBQLN4 and PAUF; ZB16B is the whole nucleotide sequence of UBQLN4. However, as the result of comparison of the peptide sequence of the UBL4A protein found as a PAUF-binding protein in the present study and the peptide sequence of the UBQL4 protein, two proteins share a Ubiquitin-like domain (FIG. 7). Therefore, it may be assumed that the Ubiquitin-like domain of UBL4A is a domain that binds with PAUF.

It has been found that the Dia1 protein plays a role when tumor cells migrate to a lower stage of the Rho signaling pathway (Cell metastasis review, 28:65-76 (2009)). The Rho signaling pathway functions in metastasis and invasion of tumor cells. The RhoC protein, which is one of three Rho proteins (RhoA, RhoB, and RhoC), is overexpressed in the lesions of pancreatic cancer patient tissue, particularly in tumor cells rather than non-malignant cells, and in metastatic lesions rather than primary tumor cells. The expression of RhoC is closely related to metastasis of tumor cells and poor prognosis of patients (Br J Cancer, 77:147-152 (1998)). The pancreatic cancer cell lines increase or inhibit the metastasis and invasion of cells depending on overexpression or inhibition of PAUF, and it is assumed that the Dia1 protein may be involved in these mechanism.

It has been reported that the SNAPIN protein is involved in exocytosis of synaptic vesicles in neuronal cells (Z. H. Sheng et al., Nat. Neurosci., 2(2):119-124 (1999)). In addition, the Soluble N-ethymaleimide-sensitive fusion protein Attachment protein REceptors (SNARE) complex was also established in the non-neuronal mammalian cells (W. Antonin et al., EMBO J., 19:6453-6464 (2000)).

It has been reported that there are several proteins in the SNAPIN binding protein. It has been reported that the SNAPIN binds to the SNAP23 protein in the non-neuronal cells (P. Buxton et al., Biochem. J., 375:433-440 (2003)). The maturity-onset diabetes of the young 3 (MODY3) in type II Diabete results from a mutation of nepatocute nuclear factor (HNF)-1a. It has been found that the protein interacting with HNF-1a is Collectrin, which is a kidney-specific gene. It has been reported that Collectrin interacts with SNAPIN to control intercellular effluence of insulin through the mechanism of the SNARE complex (K. Fukui and K. Yamagata et al., Cell metabolism, 2:373-384 (2005)). X. Yuan and Y. Cong et al. reported that the granulocyte colony-stimulating factor (G-CSF) receptor and SNAPIN interact with each other (Cytokine, 33:219-255 (2006)), and it has been reported that Exo70 and SNAPIN bind to each other to control GLUT4 vesicle trafficking (JBC, 283(1), 324-331 (2008)).

As the result of examination on whether or not PAUF is secreted in the pancreatic cancer cell lines (previous study), PAUF is secreted or not secreted according to the respective cell lines. As the result of mRNA sequence analysis, the signal sequence coding the secretion of the PAUF protein is not different according to the respective cell lines. Therefore, it is assumed that the protein involved in the procedure of migrating the secretory protein out of the cells contributes to secretion or non-secretion of PAUF, and SNAPIN is highly likely to function as a corresponding protein therefor.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An in vitro screening method comprising:
   (a) contacting in vitro a test molecule with Pancreatic Adenocarcinoma Up-regulated Factor (PAUF) comprising the sequence of SEQ ID NO:1 and a second protein comprising the sequence of SEQ ID NO:21; and
   (b) analyzing whether or not the test molecule inhibits the binding of PAUF to the second protein compared to binding of PAUF with the second protein in the absence of the test molecule.

2. The method of claim 1, wherein PAUF and the second protein are isolated and contained in a single solution in vitro.

3. The method of claim 1, wherein PAUF and the second protein are included in one isolated cell.

4. The method of claim 3, wherein the isolated cell is a cancer cell.

5. The method of claim 1, wherein the second protein comprises the sequence of SEQ ID NO:2.

6. An in vitro screening method comprising:
   (a) contacting in vitro a test molecule with Pancreatic Adenocarcinoma Up-regulated Factor (PAUF) comprising the sequence of SEQ ID NO:1 and a second protein comprising the sequence of SEQ ID NO:3; and
   (b) analyzing whether or not the test molecule inhibits the binding of PAUF to the second protein compared to binding of PAUF with the second protein in the absence of the test molecule.

7. The method of claim 6, wherein PAUF and the second protein are isolated and contained in a single solution in vitro.

8. The method of claim 6, wherein PAUF and the second protein are included in one isolated cell.

9. The method of claim 8, wherein the isolated cell is a cancer cell.

10. An in vitro screening method comprising:
    (a) contacting in vitro a test molecule with Pancreatic Adenocarcinoma Up-regulated Factor (PAUF) comprising the sequence of SEQ ID NO:1 and a second protein comprising the sequence of SEQ ID NO:4; and
    (b) analyzing whether or not the test molecule inhibits the binding of PAUF to the second protein compared to binding of PAUF with the second protein in the absence of the test molecule.

11. The method of claim 10, wherein PAUF and the second protein are isolated and contained in a single solution in vitro.

12. The method of claim 10, wherein PAUF and the second protein are included in one isolated cell.

13. The method of claim 12, wherein the isolated cell is a cancer cell.

* * * * *

SEQUENCE LISTING

```
<160> NUMBER OF SEQ ID NOS: 21

<210> SEQ ID NO 1
<211> LENGTH: 196
<212> TYPE: PRT
<213> ORGANISM: Homo sapiens

<400> SEQUENCE: 1

Met Trp Arg Val Pro Gly Thr Thr Arg Arg Pro Val Thr Gly Glu Ser
1               5                   10                  15

Pro Gly Met His Arg Pro Glu Ala Met Leu Leu Leu Thr Leu Ala
            20                  25                  30

Leu Leu Gly Gly Pro Thr Trp Ala Gly Lys Met Tyr Gly Pro Gly Gly
        35                  40                  45
```

```
Gly Lys Tyr Phe Ser Thr Thr Glu Asp Tyr Asp His Glu Ile Thr Gly
        50                  55                  60

Leu Arg Val Ser Val Gly Leu Leu Val Lys Ser Val Gln Val Lys
65                  70                  75                  80

Leu Gly Asp Ser Trp Asp Val Lys Leu Gly Ala Leu Gly Gly Asn Thr
                    85                  90                  95

Gln Glu Val Thr Leu Gln Pro Gly Glu Tyr Ile Thr Lys Val Phe Val
                100                 105                 110

Ala Phe Gln Ala Phe Leu Arg Gly Met Val Met Tyr Thr Ser Lys Asp
            115                 120                 125

Arg Tyr Phe Tyr Phe Gly Lys Leu Asp Gly Gln Ile Ser Ser Ala Tyr
        130                 135                 140

Pro Ser Gln Glu Gly Gln Val Leu Val Gly Ile Tyr Gly Gln Tyr Gln
145                 150                 155                 160

Leu Leu Gly Ile Lys Ser Ile Gly Phe Glu Trp Asn Tyr Pro Leu Glu
                165                 170                 175

Glu Pro Thr Thr Glu Pro Pro Val Asn Leu Thr Tyr Ser Ala Asn Ser
                180                 185                 190

Pro Val Gly Arg
            195

<210> SEQ ID NO 2
<211> LENGTH: 335
<212> TYPE: PRT
<213> ORGANISM: Homo sapiens

<400> SEQUENCE: 2

Met Ala Ala Gly Ala Ala Glu Ala Ala Val Ala Ala Val Glu Glu Val
1               5                   10                  15

Gly Ser Ala Gly Gln Phe Glu Glu Leu Leu Arg Leu Lys Ala Lys Ser
            20                  25                  30

Leu Leu Val Val His Phe Trp Ala Pro Trp Ala Pro Gln Cys Ala Gln
        35                  40                  45

Met Asn Glu Val Met Ala Glu Leu Ala Lys Glu Leu Pro Gln Val Ser
        50                  55                  60

Phe Val Lys Leu Glu Ala Glu Gly Val Pro Glu Val Ser Glu Lys Tyr
65                  70                  75                  80

Glu Ile Ser Ser Val Pro Thr Phe Leu Phe Phe Lys Asn Ser Gln Lys
                85                  90                  95

Ile Asp Arg Leu Asp Gly Ala His Ala Pro Glu Leu Thr Lys Lys Val
            100                 105                 110

Gln Arg His Ala Ser Ser Gly Ser Phe Leu Pro Ser Ala Asn Glu His
        115                 120                 125

Leu Lys Glu Asp Leu Asn Leu Arg Leu Lys Lys Leu Thr His Ala Ala
        130                 135                 140

Pro Cys Met Leu Phe Met Lys Gly Thr Pro Gln Glu Pro Arg Cys Gly
145                 150                 155                 160

Phe Ser Lys Gln Met Val Glu Ile Leu His Lys His Asn Ile Gln Phe
                165                 170                 175

Ser Ser Phe Asp Ile Phe Ser Asp Glu Glu Val Arg Gln Gly Leu Lys
            180                 185                 190

Ala Tyr Ser Ser Trp Pro Thr Tyr Pro Gln Leu Tyr Val Ser Gly Glu
        195                 200                 205

Leu Ile Gly Gly Leu Asp Ile Ile Lys Glu Leu Glu Ala Ser Glu Glu
        210                 215                 220
```

```
Leu Asp Thr Ile Cys Pro Lys Ala Pro Lys Leu Glu Glu Arg Leu Lys
225                 230                 235                 240

Val Leu Thr Asn Lys Ala Ser Val Met Leu Phe Met Lys Gly Asn Lys
                245                 250                 255

Gln Glu Ala Lys Cys Gly Phe Ser Lys Gln Ile Leu Glu Ile Leu Asn
            260                 265                 270

Ser Thr Gly Val Glu Tyr Glu Thr Phe Asp Ile Leu Glu Asp Glu Glu
            275                 280                 285

Val Arg Gln Gly Leu Lys Ala Tyr Ser Asn Trp Pro Thr Tyr Pro Gln
        290                 295                 300

Leu Tyr Val Lys Gly Glu Leu Val Gly Gly Leu Asp Ile Val Lys Glu
305                 310                 315                 320

Leu Lys Glu Asn Gly Glu Leu Leu Pro Ile Leu Arg Gly Glu Asn
                325                 330                 335

<210> SEQ ID NO 3
<211> LENGTH: 136
<212> TYPE: PRT
<213> ORGANISM: Homo sapiens

<400> SEQUENCE: 3

Met Ala Gly Ala Gly Ser Ala Ala Val Ser Gly Ala Gly Thr Pro Val
1               5                   10                  15

Ala Gly Pro Thr Gly Arg Asp Leu Phe Ala Glu Gly Leu Leu Glu Phe
            20                  25                  30

Leu Arg Pro Ala Val Gln Gln Leu Asp Ser His Val His Ala Val Arg
        35                  40                  45

Glu Ser Gln Val Glu Leu Arg Glu Gln Ile Asp Asn Leu Ala Thr Glu
    50                  55                  60

Leu Cys Arg Ile Asn Glu Asp Gln Lys Val Ala Leu Asp Leu Asp Pro
65                  70                  75                  80

Tyr Val Lys Lys Leu Leu Asn Ala Arg Arg Val Val Leu Val Asn
                85                  90                  95

Asn Ile Leu Gln Asn Ala Gln Glu Arg Leu Arg Arg Leu Asn His Ser
            100                 105                 110

Val Ala Lys Glu Thr Ala Arg Arg Ala Met Leu Asp Ser Gly Ile
        115                 120                 125

Tyr Pro Pro Gly Ser Pro Gly Lys
    130                 135

<210> SEQ ID NO 4
<211> LENGTH: 157
<212> TYPE: PRT
<213> ORGANISM: Homo sapiens

<400> SEQUENCE: 4

Met Gln Leu Thr Val Lys Ala Leu Gln Gly Arg Glu Cys Ser Leu Gln
1               5                   10                  15

Val Pro Glu Asp Glu Leu Val Ser Thr Leu Lys Gln Leu Val Ser Glu
            20                  25                  30

Lys Leu Asn Val Pro Val Arg Gln Gln Arg Leu Leu Phe Lys Gly Lys
        35                  40                  45

Ala Leu Ala Asp Gly Lys Arg Leu Ser Asp Tyr Ser Ile Gly Pro Asn
    50                  55                  60

Ser Lys Leu Asn Leu Val Val Lys Pro Leu Glu Lys Val Leu Leu Glu
65                  70                  75                  80
```

Glu Gly Glu Ala Gln Arg Leu Ala Asp Ser Pro Pro Gln Val Trp
                85                  90                  95

Gln Leu Ile Ser Lys Val Leu Ala Arg His Phe Ser Ala Ala Asp Ala
            100                 105                 110

Ser Arg Val Leu Glu Gln Leu Gln Arg Asp Tyr Glu Arg Ser Leu Ser
        115                 120                 125

Arg Leu Thr Leu Asp Asp Ile Glu Arg Leu Ala Ser Arg Phe Leu His
    130                 135                 140

Pro Glu Val Thr Glu Thr Met Glu Lys Gly Phe Ser Lys
145                 150                 155

```
<210> SEQ ID NO 5
<211> LENGTH: 26
<212> TYPE: DNA
<213> ORGANISM: Artificial Sequence
<220> FEATURE:
<223> OTHER INFORMATION: pGBKT7-PAUF primer (forward)

<400> SEQUENCE: 5
cccgccatgg cgatgtggag ggtgcc                                         26

<210> SEQ ID NO 6
<211> LENGTH: 27
<212> TYPE: DNA
<213> ORGANISM: Artificial Sequence
<220> FEATURE:
<223> OTHER INFORMATION: pGBKT7-PAUF Primer (Reverse)

<400> SEQUENCE: 6
gcccgaattc gcgacccacg ggtgagt                                        27

<210> SEQ ID NO 7
<211> LENGTH: 30
<212> TYPE: DNA
<213> ORGANISM: Artificial Sequence
<220> FEATURE:
<223> OTHER INFORMATION: 3xFLAG-CMV14/H13 (SNAPIN) Primer (forward)

<400> SEQUENCE: 7
cccaagcttg ggatggcggg ggctggttcc                                     30

<210> SEQ ID NO 8
<211> LENGTH: 31
<212> TYPE: DNA
<213> ORGANISM: Artificial Sequence
<220> FEATURE:
<223> OTHER INFORMATION: 3xFLAG-CMV14/H13 (SNAPIN) Primer (Reverse)

<400> SEQUENCE: 8
cgcggatccg cgtttgcctg gggagccagg g                                   31

<210> SEQ ID NO 9
<211> LENGTH: 28
<212> TYPE: DNA
<213> ORGANISM: Artificial Sequence
<220> FEATURE:
<223> OTHER INFORMATION: 3xFLAG-CMV14/H14 (GLRX3) Primer (forward)

<400> SEQUENCE: 9
aatgcggccg cagcatggcg gcggggc                                        28

<210> SEQ ID NO 10
<211> LENGTH: 37
```

<212> TYPE: DNA
<213> ORGANISM: Artificial Sequence
<220> FEATURE:
<223> OTHER INFORMATION: 3xFLAG-CMV14/H14 (GLRX3) Primer (Reverse)

<400> SEQUENCE: 10
cgcggatccg cgattttctc ctctcagtat aggcagc                              37

<210> SEQ ID NO 11
<211> LENGTH: 28
<212> TYPE: DNA
<213> ORGANISM: Artificial Sequence
<220> FEATURE:
<223> OTHER INFORMATION: 3xFLAG-CMV14/H14N (GLRX3N) Primer (forward)

<400> SEQUENCE: 11
aatgcggccg cagcatggcg gcgggggc                                        28

<210> SEQ ID NO 12
<211> LENGTH: 32
<212> TYPE: DNA
<213> ORGANISM: Artificial Sequence
<220> FEATURE:
<223> OTHER INFORMATION: 3xFLAG-CMV14/H14N (GLRX3N) Primer (reverse)

<400> SEQUENCE: 12
cgcggatccg caggggggcag catgagtcaa tt                                  32

<210> SEQ ID NO 13
<211> LENGTH: 39
<212> TYPE: DNA
<213> ORGANISM: Artificial Sequence
<220> FEATURE:
<223> OTHER INFORMATION: 3xFLAG-CMV14/H14C (GLRX3C) Primer (forward)

<400> SEQUENCE: 13
aatgcggccg catgaacctt cgcttgaaga aattgactc                            39

<210> SEQ ID NO 14
<211> LENGTH: 37
<212> TYPE: DNA
<213> ORGANISM: Artificial Sequence
<220> FEATURE:
<223> OTHER INFORMATION: 3xFLAG-CMV14/H14C (GLRX3C) Primer (reverse)

<400> SEQUENCE: 14
cgcggatccg cgattttctc ctctcagtat aggcagc                              37

<210> SEQ ID NO 15
<211> LENGTH: 30
<212> TYPE: DNA
<213> ORGANISM: Artificial Sequence
<220> FEATURE:
<223> OTHER INFORMATION: 3xFLAG-CMV14/H32 (UBL4A) Primer (forward)

<400> SEQUENCE: 15
cccaagcttg ggatgcagct gacggtgaaa                                      30

<210> SEQ ID NO 16
<211> LENGTH: 32
<212> TYPE: DNA
<213> ORGANISM: Artificial Sequence
<220> FEATURE:
<223> OTHER INFORMATION: 3xFLAG-CMV14/H32 (UBL4A) Primer (reverse)

<400> SEQUENCE: 16
cgcggatccg cgtttggaga agcccttctc ca                                        32

<210> SEQ ID NO 17
<211> LENGTH: 17
<212> TYPE: DNA
<213> ORGANISM: Artificial Sequence
<220> FEATURE:
<223> OTHER INFORMATION: GLRX3 forward primer

<400> SEQUENCE: 17
gggcggctga ggcagct                                                         17

<210> SEQ ID NO 18
<211> LENGTH: 19
<212> TYPE: DNA
<213> ORGANISM: Artificial Sequence
<220> FEATURE:
<223> OTHER INFORMATION: GLRX3 reverse primer

<400> SEQUENCE: 18 gcaggggca gcatgagtc                                                        19

<210> SEQ ID NO 19
<211> LENGTH: 20
<212> TYPE: DNA
<213> ORGANISM: Artificial Sequence
<220> FEATURE:
<223> OTHER INFORMATION: ACTB forward primer

<400> SEQUENCE: 19
ggcatcctca ccctgaagta                                                      20

<210> SEQ ID NO 20
<211> LENGTH: 20
<212> TYPE: DNA
<213> ORGANISM: Artificial Sequence
<220> FEATURE:
<223> OTHER INFORMATION: ACTB reverse primer

<400> SEQUENCE: 20
ggggtgttga aggtctcaaa                                                      20

<210> SEQ ID NO 21
<211> LENGTH: 146
<212> TYPE: PRT
<213> ORGANISM: Homo sapiens

<400> SEQUENCE: 21

Met Ala Ala Gly Ala Ala Glu Ala Ala Val Ala Ala Val Glu Glu Val
1               5                   10                  15

Gly Ser Ala Gly Gln Phe Glu Glu Leu Leu Arg Leu Lys Ala Lys Ser
            20                  25                  30

Leu Leu Val Val His Phe Trp Ala Pro Trp Ala Pro Gln Cys Ala Gln
        35                  40                  45

Met Asn Glu Val Met Ala Glu Leu Ala Lys Glu Leu Pro Gln Val Ser
    50                  55                  60

Phe Val Lys Leu Glu Ala Glu Gly Val Pro Glu Val Ser Glu Lys Tyr
65                  70                  75                  80

Glu Ile Ser Ser Val Pro Thr Phe Leu Phe Phe Lys Asn Ser Gln Lys
                85                  90                  95

Ile Asp Arg Leu Asp Gly Ala His Ala Pro Glu Leu Thr Lys Lys Val
            100                 105                 110

-continued

```
Gln Arg His Ala Ser Ser Gly Ser Phe Leu Pro Ser Ala Asn Glu His
        115                 120                 125

Leu Lys Glu Asp Leu Asn Leu Arg Leu Lys Lys Leu Thr His Ala Ala
    130                 135                 140

Pro Cys
145
```